United States Patent
Malowaniec

(10) Patent No.: US 6,630,611 B1
(45) Date of Patent: Oct. 7, 2003

(54) ABSORBENT ELEMENTS FOR HYGIENE ARTICLES

(75) Inventor: Krzysztof Malowaniec, Heidenheim (DE)

(73) Assignee: Paul Hartmann AG (DE)

( * ) Notice: Subject to any disclaimer, the term of this patent is extended or adjusted under 35 U.S.C. 154(b) by 0 days.

(21) Appl. No.: 09/890,780

(22) PCT Filed: Nov. 27, 1999

(86) PCT No.: PCT/EP99/09232

§ 371 (c)(1),
(2), (4) Date: Aug. 6, 2001

(87) PCT Pub. No.: WO00/47150

PCT Pub. Date: Aug. 17, 2000

(30) Foreign Application Priority Data

Feb. 8, 1999 (EP) .............................. 99101688

(51) Int. Cl.[7] .............................. A61F 13/15
(52) U.S. Cl. ..................... 604/375; 604/374
(58) Field of Search ................. 604/374, 375, 604/378, 380, 385.101, 383

(56) References Cited

U.S. PATENT DOCUMENTS

| | | | | | |
|---|---|---|---|---|---|
| 4,676,786 | A | * | 6/1987 | Nishino | 604/378 |
| 4,699,823 | A | * | 10/1987 | Kellenberger et al. | 428/219 |
| 5,183,707 | A | * | 2/1993 | Herron et al. | 428/364 |
| 5,531,728 | A | * | 7/1996 | Lash | 604/378 |
| 5,549,791 | A | * | 8/1996 | Herron et al. | 162/157.6 |
| 5,558,655 | A | * | 9/1996 | Jezzi et al. | 604/378 |
| 5,589,117 | A | * | 12/1996 | Yang | 264/113 |
| 5,669,895 | A | * | 9/1997 | Murakami et al. | 604/380 |
| 5,728,082 | A | * | 3/1998 | Gustafsson et al. | 604/368 |
| 5,891,120 | A | * | 4/1999 | Chmielewski | 604/378 |
| 5,895,379 | A | * | 4/1999 | Litchholt et al. | 604/378 |
| 5,961,505 | A | * | 10/1999 | Coe et al. | 604/378 |
| 6,206,865 | B1 | * | 3/2001 | Chen et al. | 604/385.01 |
| 6,323,387 | B1 | * | 11/2001 | Soga et al. | 604/368 |

FOREIGN PATENT DOCUMENTS

| | | |
|---|---|---|
| GB | 2 215 609 | 9/1989 |
| WO | WO 91 10416 | 7/1991 |
| WO | WO 93 15702 | 8/1993 |
| WO | WO 95 13042 | 5/1995 |

* cited by examiner

Primary Examiner—Weilun Lo
Assistant Examiner—Jacqueline Stephens
(74) Attorney, Agent, or Firm—Young & Basile, PC

(57) ABSTRACT

An absorbent element for a disposable absorbent hygiene article for absorbing and storing body fluids, notably urine. The element includes an absorbent and distributing layer which, during use, is situated in proximity to the body and contains internally cross-linked cellulose fibers, and a storage layer which, during use, is situated away from the body and contains natural, non-cross-linked cellulose fibers and superabsorbant materials. The horizontal expansion of the absorbent and distributing layer situated close to the body is less than that of the storage layer and in all directions does not extend beyond the edges of the storage layer. The absorbent and distributing layer consists of internally cross-linked cellulose fibers having a first retention value of between 0.6 and 0.9 $g_{fl/Fiber}$ and between 8 and 15% by weight superabsorbant polymer materials and the storage layer consists of non-cross-linked cellulose fibers having a second retention value of between 1.0 and 1.4 $g_{fl/Fiber}$ and of at least 20% by weight superabsorbant polymer materials.

5 Claims, 1 Drawing Sheet

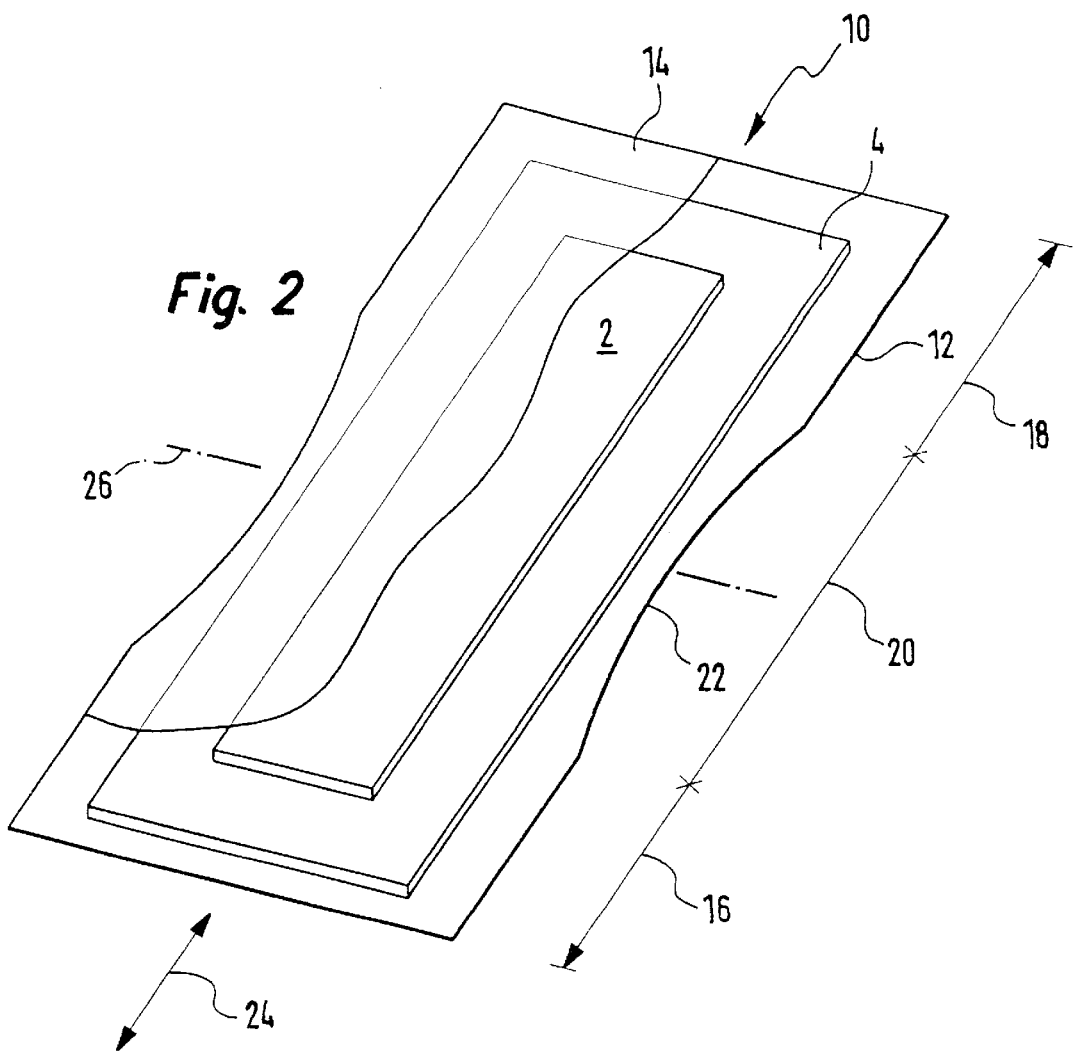

ABSORBENT ELEMENTS FOR HYGIENE ARTICLES

BACKGROUND

The invention relates to an absorbent element for an absorptive hygiene article for one-time use for absorbing and storing bodily fluids, specifically urine, with an absorption and dispersion layer placed next to the body in use of intra-meshed cellulose fibers, and with a retaining layer placed away from the body of natural non-meshed cellulose fibers and superabsorbent materials, where the surface expanse of the absorption and dispersion layer next to the body is smaller than that of the retaining layer and is located within the border of the retention layer in all directions.

This type of construction for an absorbent element is known, for example, from WO-A-91/11193. This publication teaches fashioning the absorption and dispersion layer next to the body so that it comprises 50 to 100-percent by weight intra-meshed cellulose fibers and 0 to 50 percent by weight of binder for these fibers. The absorption and dispersion layer is preferably supposed to be free of superabsorbent materials. The embodiments reveal an absorption layer and a dispersion layer of 92 percent by weight intra-meshed cellulose fibers and 8 percent by weight non-meshed cellulose fibers; a further embodiment of an absorption and dispersion layer which consists 100-percent of intra-meshed cellulose fibers, as well as an embodiment with an absorption and dispersion layer which comprises 55 percent by weight intra-meshed cellulose fibers and 45 percent by weight thermoplastic polypropylene microfibers, where the latter make up the binder. In all the embodiments, in accordance with the teaching of the publication, there are no superabsorbent materials contained in the absorption and dispersion layer.

A non-generic absorbent element structure is known from GB-A-2 215 609, according to which the upper absorption and dispersion layer basically extends across the entire surface area of a hygiene article and completely covers a comparatively much smaller layer, which, according to the doctrine of this publication, is placed principally in the front area of the hygiene article and there it provides a locally high absorption capacity. The fiber portion of both layers consists of intra-meshed cellulose fibers.

The periodical teaches accordingly a very special arrangement through localized concentration of superabsorbent materials.

SUMMARY

The present invention desires to improve the reverse wetting characteristics in an absorbent element of the type described above. Under compressive load on an absorbent element of a hygiene article, for example when sitting, fluid contained in the absorption and dispersion layer which was not routed into the absorbent element located underneath can reach the surface of the user's skin and cause a sensation of wetness which is experienced as an unpleasant sensation. The absorbent element is intended to be constructed in an economical fashion and as simply as possible.

The invention is also an absorptive hygiene article for one-time use with a fluid-tight backing, a fluid-permeable cover and an absorbent element positioned between them, which is characterized in that the absorbent element is designed in accordance with the present invention and the retention layer of the absorbent element extends uniformly over the front, rear and crotch area of the hygiene article, so that it is positioned approximately symmetrically to a center transverse line of the crotch area.

BRIEF DESCRIPTION OF THE DRAWING

Additional features, details and advantages of the invention can be derived from the attached patent claims and from the graphical representation and subsequent description of a preferred embodiment of an absorbent element according to the invention. In the drawing:

FIG. 1 is a schematic sectional view of an absorbent element according to the invention; and FIG. 2 is a schematic perspective view of a hygiene article.

DETAILED DESCRIPTION

FIGS. 1 and 2 show an absorbent element according to the invention consisting of an absorption and dispersion layer 2 which faces the body when used in a hygiene article and a retention layer 4. The absorption and dispersion layer 2 consists of intra-meshed natural cellulose fibers with 8 to 12 percent by weight of a superabsorbent polymer material. The retention layer 4 is formed from non-meshed natural cellulose fibers, preferably of the same type with a retention value of between 1.0 and 1.4 $g_{fl}/g_{fibe,r}$ and at least 20 percent by weight of a superabsorbent polymer material. The retention layer 4 comprises a split layer 6, containing SAP and facing the absorption and dispersion layer 2, and an SAP-free split layer 8, which faces away from the body in use.

FIG. 2 shows a hygiene article identified overall with the reference numeral 10 in the form of a diaper with a fluid-tight backing 12, a merely indicated fluid-permeable cover 14 and an absorbent element positioned between them, consisting of retention layer 4 positioned away from the body and absorption layer 2 ending up next to the body, which are shaped as described previously in conjunction with FIG. 1. It can be seen that the retention layer 4 extends uniformly over a front 16, rear 18 and crotch area 20 of the hygiene article, where the crotch area 20 is identified and considered as that area along which openings for the legs 22 extend in the longitudinal direction 24 of the hygiene article. Accordingly, this area is formed as far as the retention area 4, symmetrically to a transverse line 26 running centrally as a symmetrical axis.

In the case of an absorbent element of the type described above in accordance with the invention by having the absorption and dispersion layer consist of intra-meshed cellulose fibers with a secondary retention value between 0.6 and 0.9 $g_{fl}/g_{fiber}$ and 8–15 percent by weight of superabsorbent polymer materials and having the retention layer consist of non-meshed cellulose fibers with a primary retention value between 1.0 and 1.4 $g_{fl}/g_{fiber}$ and at least 20 percent by weight superabsorbent polymer materials.

The dual-layer absorbent element is of particularly simple design and is therefore easily easy to produce because the fiber portion of the absorption and dispersion layer consists of intra-meshed natural cellulose fibers and that of the retention layer of non-meshed natural cellulose fibers. The single other component is a superabsorbent polymer material. The retention value of the fibers is determined according to a procedure to be described subsequently. It was found that through the use of superabsorbent materials in a proportion of 8–15 percent by weight, preferably 8 to 12 percent by weight, specifically 10 to 12 percent by weight in the absorption and dispersion layer and with the previously mentioned choice of the amount of fiber, very good absorption and dispersion performance for the layer facing the body, as well as outstanding reverse wetting characteristics, were achieved. An advantageous volume of pores in the absorption and dispersion layer facing the body is achieved even in a wet state due to the proportion of fibers in the form of intra-meshed natural cellulose fibers. Intra-meshed natural cellulose fibers have the property of swelling when exposed to fluid so that their density is reduced when wetted, which means that the individual fibers occupy a greater volume. As a result of these processes, the volume of pores and thereby the fluid absorption rate is increased.

It was discovered in accordance with the invention that this process is supported by a relatively high proportion of superabsorbent materials in the absorption and dispersion layer, as the result of the swelling characteristics of the superabsorbent materials, which help to separate the fibers from one another and swell them. The pore volume is even more substantially enlarged, which in turn results in an even greater absorption capacity during the influx of fluid. The combination of a relatively high SAP content in conjunction with meshed natural cellulose fibers with a retention value between 0.6 and 0.9 $g_{fl}/g_{fiber}$ results in the dreaded gel blocking, which was suspected in the prior art in connection with elevated SAP contents, not taking place. However, if the absorption and dispersion layer comprise only a low or no amount of superabsorbent materials, the residual water content of this layer and consequently the reverse wetting performance is not satisfactory. Reverse wetting performance is substantially improved through the structure of the absorbent element according to the invention. Fluid remaining in the absorption and dispersion layer is effectively and completely bound as a result of the high superabsorbent materials content, and when pressure is exerted on the absorbent element, no fluid is pressed against the user's skin.

The fluid retention ability of the meshed and non-meshed natural cellulose fibers is determined by the following centrifuge test by indicating the retention value. A layer of cellulose fibers to be studied is weighed in its dry state to determine its mass in grams. The specimens are then completely immersed for 30 minutes in a 1-percent sodium chloride solution of demineralized water as the test solution and afterwards spun for 4 minutes at 276 times the speed of gravitational acceleration. Then the specimens are weighed again to determine their mass, including the bound fluid. The mass of the absorbed or bound fluid is derived from the difference between the mass determined after being spun and the dry mass of the fiber material being studied. If this difference is divided by the dry mass, the retention value in $g_{fl}/g_{fiber}$ is obtained.

What is claimed is:

1. An absorbent element for an absorptive hygiene article for one-time use for absorbing and holding bodily fluids with an absorption and dispersion layer located next to the body in use, having intra-crosslinked cellulose fibers and having a retention layer with natural, non-meshed cellulose fibers and superabsorbent materials located away from the body in use, where the surface expanse of the absorption and dispersion layer next to the body is smaller than that of the retention layer and is positioned in all directions within a border of the retention layer, characterized in that the absorption and dispersion layer is formed of intra-crosslinked cellulose fibers with a primary retention value between 0.6 and 0.9 $g_{fl}/g_{fiber}$ and 8 to 15 percent by weight of superabsorbent polymer materials, and the retention layer is formed of non-meshed cellulose fibers with a secondary retention value between 1.0 and 1.4 $g_{fl}/g_{fiber}$ and at least 20 percent by weight of superabsorbent polymer materials.

2. The absorbent element in accordance with claim 1, wherein the absorption and dispersion layer next to the body consists of 8 to 12 percent by weight of superabsorbent polymer materials.

3. The absorbent element in accordance with claim 2, wherein the absorption layer next to the body consists of 10 to 12 percent by weight of superabsorbent polymaterials.

4. The absorbent element in accordance with claim 1, wherein the retention layer has a split layer on the side facing away from the absorption and dispersion layer, which is free of superabsorbent materials.

5. An absorptive hygiene article for one time use with a front area, a rear area, and a crotch area lying there between, with a fluid-tight backing, a fluid-permeable cover and an absorbent element positioned there between, wherein the absorbent element is fashioned in accordance with claim 1 and the retention layer of the absorbent element extends uniformly over front, rear and crotch area of the hygiene article.

* * * * *